United States Patent
Henao et al.

(10) Patent No.: US 9,828,308 B2
(45) Date of Patent: *Nov. 28, 2017

(54) HYDROCARBON CONVERSION

(71) Applicant: ExxonMobil Chemical Patents Inc., Baytown, TX (US)

(72) Inventors: Juan D. Henao, Houston, TX (US); Paul F. Keusenkothen, Houston, TX (US); Abhimanyu O. Patil, Westfield, NJ (US)

(73) Assignee: ExxonMobil Chemical Patents Inc., Baytown, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 15/593,847

(22) Filed: May 12, 2017

(65) Prior Publication Data

US 2017/0247299 A1  Aug. 31, 2017

Related U.S. Application Data

(62) Division of application No. 14/543,243, filed on Nov. 17, 2014.

(60) Provisional application No. 61/912,877, filed on Dec. 6, 2013.

(30) Foreign Application Priority Data

Feb. 5, 2014  (EP) .................... 14153941

(51) Int. Cl.
*C07C 2/76* (2006.01)
*C07C 2/84* (2006.01)
*C07C 2/58* (2006.01)

(52) U.S. Cl.
CPC . *C07C 2/84* (2013.01); *C07C 2/58* (2013.01)

(58) Field of Classification Search
None
See application file for complete search history.

(56) References Cited

U.S. PATENT DOCUMENTS

| | | |
|---|---|---|
| 3,700,585 A | 10/1972 | Chen et al. |
| 3,702,886 A | 11/1972 | Argauer et al. |
| 3,709,979 A | 1/1973 | Chu et al. |
| 3,832,449 A | 8/1974 | Rosinski et al. |
| 3,911,041 A | 10/1975 | Kaeding et al. |
| 3,928,483 A | 12/1975 | Chang et al. |
| 3,931,349 A | 1/1976 | Kuo |

(Continued)

FOREIGN PATENT DOCUMENTS

| | | |
|---|---|---|
| CN | 101244969 A | 8/2008 |
| EP | 0293032 B | 7/1993 |

(Continued)

OTHER PUBLICATIONS

Skutil et al., Some technological aspetcs of methane aromatization (direct and via oxidative coupling), Fuel Processing TEchnology 87, 2006, pp. 511-521.*

(Continued)

*Primary Examiner* — Philip Louie

(57) ABSTRACT

This invention relates to the conversion of substantially-saturated hydrocarbon to higher-value hydrocarbon products such as aromatics and/or oligomers, to equipment and materials useful in such conversion, and to the use of such conversion for, e.g., natural gas upgrading.

4 Claims, 2 Drawing Sheets

(56) References Cited

U.S. PATENT DOCUMENTS

| | | | |
|---|---|---|---|
| 4,016,218 A | 4/1977 | Haag et al. | |
| 4,016,245 A | 4/1977 | Plank et al. | |
| 4,046,825 A | 9/1977 | Owen et al. | |
| 4,049,573 A | 9/1977 | Kaeding | |
| 4,062,905 A | 12/1977 | Chang et al. | |
| 4,076,842 A | 2/1978 | Plank et al. | |
| 4,079,095 A | 3/1978 | Givens et al. | |
| 4,079,096 A | 3/1978 | Givens et al. | |
| 4,088,706 A | 5/1978 | Kaeding | |
| 4,111,847 A | 9/1978 | Stiles | |
| 4,138,440 A | 2/1979 | Chang et al. | |
| RE29,948 E | 3/1979 | Dwyer et al. | |
| 4,229,424 A | 10/1980 | Kokotailo | |
| 4,234,231 A | 11/1980 | Yan | |
| 4,424,401 A | 1/1984 | White et al. | |
| 4,439,409 A | 3/1984 | Puppe et al. | |
| 4,440,871 A | 4/1984 | Lok et al. | |
| 4,499,327 A | 2/1985 | Kaiser | |
| 4,556,477 A | 12/1985 | Dwyer | |
| 4,826,667 A | 5/1989 | Zones et al. | |
| 4,873,067 A | 10/1989 | Valyocsik et al. | |
| 4,954,325 A | 9/1990 | Rubin et al. | |
| 4,968,655 A * | 11/1990 | Jezl | C07C 2/84 502/241 |
| 5,012,029 A | 4/1991 | Han et al. | |
| 5,236,575 A | 8/1993 | Bennett et al. | |
| 5,250,277 A | 10/1993 | Kresge et al. | |
| 5,336,825 A | 8/1994 | Choudhary et al. | |
| 5,362,697 A | 11/1994 | Fung et al. | |
| 5,370,851 A | 12/1994 | Wilson | |
| 5,633,417 A | 5/1997 | Beck et al. | |
| 5,675,047 A | 10/1997 | Beck et al. | |
| 5,936,135 A | 8/1999 | Choudhary et al. | |
| 6,077,498 A | 6/2000 | Cabanas et al. | |
| 6,200,536 B1 | 3/2001 | Tonkovich et al. | |
| 6,219,973 B1 | 4/2001 | Lafferty | |
| 6,365,792 B1 | 4/2002 | Stapf et al. | |
| 6,518,475 B2 | 2/2003 | Fung et al. | |
| 6,756,030 B1 | 6/2004 | Rohde et al. | |
| 7,014,807 B2 | 3/2006 | O'Brien | |
| 7,015,369 B2 | 3/2006 | Hack et al. | |
| 7,022,888 B2 | 4/2006 | Choudhary et al. | |
| 7,453,018 B2 | 11/2008 | Dakka et al. | |
| 7,799,962 B2 | 9/2010 | Dakka et al. | |
| 7,977,519 B2 | 7/2011 | Iaccino et al. | |
| 8,119,076 B2 | 2/2012 | Keusenkothen et al. | |
| 8,138,384 B2 | 3/2012 | Iaccino et al. | |
| 8,552,247 B2 | 10/2013 | Noe et al. | |
| 2004/0192990 A1 | 9/2004 | Choudhary et al. | |
| 2005/0107481 A1 | 1/2005 | Osborn | |
| 2006/0149109 A1 | 7/2006 | Ruziska et al. | |
| 2007/0161717 A1 | 7/2007 | Hu et al. | |
| 2007/0249879 A1 | 10/2007 | Iaccino et al. | |
| 2007/0259972 A1 | 11/2007 | Lattner et al. | |
| 2008/0033218 A1 | 2/2008 | Lattner et al. | |
| 2008/0293980 A1 | 11/2008 | Kiesslich et al. | |
| 2010/0305221 A1 | 12/2010 | Schunk et al. | |
| 2012/0115965 A1 | 1/2012 | Olah et al. | |
| 2012/0083637 A1 | 4/2012 | Clem et al. | |
| 2013/0023709 A1 | 1/2013 | Cizeron et al. | |
| 2013/0253079 A1 | 9/2013 | Jothimurugesan et al. | |

FOREIGN PATENT DOCUMENTS

| | | |
|---|---|---|
| EP | 1704132 A | 7/2005 |
| EP | 2184269 A | 5/2010 |
| GB | 2191212 A | 12/1987 |
| WO | 97/17290 A | 5/1997 |
| WO | 2004/087624 A | 10/2004 |
| WO | 2012/099674 A | 7/2012 |

OTHER PUBLICATIONS

Chemical and Engineering News, vol. 63, No. 5, pp. 27 (1985).
Chemistry Letters, vol. 35, No. 2, pp. 142-147, 2006.
Catalysis Letters, vol. 28, pp. 241-248, (1994).
Centi et al, "Direct Conversion of Methane, Ethane, and Carbon Dioxide to Fuels and Chemicals", The Catalyst Group Resources Inc., Spring House, 2008.
Navarro et al., Chem. Rev., vol. 107, pp. 3952, 2007.
Choudhary, et al., Science, vol. 275, pp. 1286-1288, 1997.
Choudhary et al., Microporous and Mesoporous Materials, vol. 23, pp. 231-238, 1998.
Guo et al., Journal of Molecular Catalysis A: Chemical, vol. 239, pp. 222-227, 2005.
Guo et al., Journal of Natural Gas Chemistry, vol. 18, pp. 260-272, 2009.
Anunziata, et al., Applied Catalysis A: General, vol. 190, pp. 169-176, 2000.
Ammar et al., "Conversion of mixtures of methane and ethylene or acetylene into liquids", Pre-Pring Archive—Amer. Inst. of Chem Engr., Spring National Meeting, New Orleans, LA USA, Mar. 11-14, 2001, Proceedings of the Second Topical Conference on Natural Gas Utilization, American Institute of Chemical Engineer, Jan. 1, 2002 (Jan. 1, 2002) p. 416, paragraph 3, figure 4.
Li et al., "A process for a high yield of aromatics from the oxygen-free conversion of methane: combining plasma with Ni/HZSM-5 catalysts", Green Chemistry, vol. 9, No. 6, Jan. 1, 2007 92007-01-01), p. 647, col. 2, last paragraph, p. 650, col. 2, paragraph 1: figures 1-3.
Ha, "Aromatization of methane over zeolite supported molybdenum: active sites and reaction mechanism", Journal of Molecular Catalysis A: Chemical, vol. 181, No. 1-2, Mar. 25, 2002, pp. 283-290.
Anunziata, Catalysis Letters, vol. 87, No. 3/4, Jan. 1, 2003, pp. 167-171.
Hu et al., "Conversion of biomass-derived syngas to alcohols and C2 oxygenates, using supported Rh catalysts in a microchannel reactor", Jan. 30, 2007, Catalysis Today, vol. 120, pp. 90-95.
Yagita et al., Environmental Catalysis, G. Centi et al. Eds. SCI Publication, Rome, 1995, pp. 639-642.
Galvis et al., "Iron Particle Size Effects for Direct Production of Lower Olefins for Synthesis Gas", Journal of American Chemical Society, Sep. 6, 2012.
Galvis et al., "Supported Iron Nanoparticles as Catalysts for Sustainable Production of Lower Olefins", Feb. 17, 2012, Science, vol. 6070, pp. 835-838.
Spivey et al., "Heterogeneous Catalytic Synthesis of Ethanol from Biomass-Derived Syngas", Mar. 7, 2007, Chemical Society Reviews, vol. 38, pp. 1514-1515.
Knifton, "Ruthenium Melt Catalysis", Producing Chemicals from Synthetic Gas, Austin Texas s.n., vol. 29, pp. 63, 1985.
Choudhary et al., Angew Chem. Int. Ed., 2005, vol. 44, pp. 4381-4385.
Aderson, Appl. Catal. vol. 47, (1989) p. 177.
Lee et al., Catal. Rev. Sci. Eng., vol. 30 (1988) pp. 249.
Hutchings et al., Chem. Soc. Rev., vol. 18 (1989), pp. 25.
Science 153, (1966), pp. 1393, "High Temperature Synthesis of Aromatics Hydrocarbons from Methane".
Lunsford, Ang. Chem. Intl. Ed. Engl. vol. 24, (1995), pp. 970.
Haggin, Methane to Gasoline Plant Adds to New Zealand Liquid Fuel Resources, Chemical & Engineering News, pp. 22, Jun. 22, 1987.
Lunsford, The Catalytic Conversion of Methane to Higher Hydrocarbons, Catal. Today, vol. 6, p. 235, 1990.
Fujimoto et al, Synthesis gas conversion utilizing mixed catalyst composed of CO reducing catalyst and solid acid: II. Direct synthesis of aromatic hydrocarbons from synthesis gas, May 1984, Journal of Catalysis, vol. 87, Issue 1, pp. 136-143.
Inoue et al., "Selective Conversion of Methanol into Aromatic Hydrocarbons Over Silver Exchanged ZAM-5 Zeolites", Elsevier, 1995, Microporous Materials, vol. 4, pp. 379-383.
Majhi et al., "Direct conversion of methane with methanol toward higher hydrocarbon over GA modified Mo/H-ZSM-5 catalyst", Journal of Industrial and Engineering Chemistry, vol. 20, No. 4, Oct. 14, 2013, pp. 2364-2369.

(56) References Cited

OTHER PUBLICATIONS

Anunziata et al., "Methane transformation into aromatic hydrocarbons by activiation with LPG over Zn-ZSM-11 Zeolite", Catalysis Letters, Springer New York LLC, United States, vol. 58, No. 4, Apr. 1, 1999, pp. 235-239.

Zhang et al., "Aromatization of Methane in the absence of oxygen over mo-based catalysts supported on different types of zeolites", Catalysis Letters, vol. 56, No. 4, Jan. 1, 1999, pp. 207-213.

Bijani et al., "Nonoxidative Aromatization of CH 4 using C3H8 as a Coreactant: Thermodynamic and Experimental Analysis", Industrial and Engineering Chemistry Research, vol. 53, No. 2, Jan. 15, 2014, pp. 572-581.

Ghose et al., Applied Catalysis A: General, vol. 452, (2013), pp. 147-154.

Kondratenko et al., Handbook of Heterogeneous Catalysis, vol. 6, (2008), pp. 3010-3023.

\* cited by examiner

HYDROCARBON CONVERSION

CROSS REFERENCE TO RELATED APPLICATIONS

This application is a divisional of U.S. patent application Ser. No. 14/543,243, filed Nov. 17, 2014, which claims priority to Provisional U.S. Patent Application Ser. No. 61/912,877, filed Dec. 6, 2013, the disclosures of which are incorporated herein by reference in their entireties. This application also claims priority to European Patent Application No. EP 14153941.1, filed Feb. 5, 2014, the disclosure of which is incorporated herein by reference in its entirety. Cross reference is made to the following related patent applications: (i) P.C.T. Patent Application No. PCT/US2014/065947, filed Nov. 17, 2014; (ii) U.S. patent application Ser. No. 14/543,271, filed Nov. 17, 2014; (iii) P.C.T. Patent Application No. PCT/US2014/065956, filed Nov. 17, 2014; (iv) U.S. patent application Ser. No. 14/543,365, filed Nov. 17, 2014; (v) P.C.T. Patent Application No. PCT/US2014/065969, filed Nov. 17, 2014; (vi) U.S. patent application Ser. No. 14/543,426, filed Nov. 17, 2014; (vii) P.C.T. Patent Application No. PCT/US2014/065961, filed Nov. 17, 2014; and (viii) U.S. patent application Ser. No. 14/543,405, filed Nov. 17, 2014.

FIELD

This disclosure relates to the conversion of substantially-saturated hydrocarbon to higher-value hydrocarbon products such as aromatics, to equipment and materials useful in such conversion, and to the use of such conversion for, e.g., natural gas upgrading.

BACKGROUND

Although methane is abundant, its relative inertness has limited its utility in conversion processes for producing higher-value hydrocarbons. For example, oxidative coupling methods generally involve highly exothermic and potentially hazardous methane combustion reactions, frequently require expensive oxygen generation facilities and produce large quantities of environmentally sensitive carbon oxides. In addition, non-oxidative methane aromatization is equilibrium-limited, and temperatures ≥ about 800° C. are needed for methane conversions greater than a few percent.

To obviate this problem, catalytic processes have been proposed for co-converting methane and one or more co-reactants to higher hydrocarbons, such as aromatics. For example, U.S. Pat. No. 5,936,135 discloses reacting methane at a temperature in the range of 300° C. to 600° C. with (i) a $C_{2-10}$ olefin and/or (ii) a $C_{2-10}$ paraffin in the presence of a bifunctional pentasil zeolite catalyst, having strong dehydrogenation and acid sites, to produce aromatics. The preferred mole ratio of olefin and/or higher paraffin to methane and/or ethane in the feed ranges from about 0.2 to about 2.0.

Other processes utilize organic oxygenate as a co-reactant for the non-oxidative methane conversion to produce higher hydrocarbons, including aromatics. For example, U.S. Pat. No. 7,022,888 discloses a process for the non-oxidative conversion of methane simultaneously with the conversion of an organic oxygenate, represented by a general formula: $C_nH_{2n+1}OC_mH_{2m+1}$, wherein C, H and O are carbon, hydrogen and oxygen, respectively; n is an integer having a value between 1 and 4; and m is an integer having a value between zero and 4, to $C_{2+}$ hydrocarbons, particularly to gasoline range $C_6$-$C_{10}$ hydrocarbons and hydrogen, using a bifunctional pentasil zeolite catalyst, having strong acid and dehydrogenation functions, at a temperature below 700° C.

There is, however, interest in developing alternative routes for the conversion of methane into aromatics and particularly routes that allow more methane to be incorporated into the aromatic product and that allows a broader molar ratio range of methane to co-reactant in the feed.

SUMMARY

It has now been found that using acetylene as the co-reactant allows substantially-saturated hydrocarbon, such as one or more of methane, ethane, propanes, butanes, pentanes, etc., to be converted to aromatics and/or oligomers. The aromatics products are generally rich in toluene and xylenes. The conversion can generally be carried out at relatively low temperature compared to conventional processes, and with a lesser amount of co-reactant per unit weight of aromatics produced. In some aspects, the substantially-saturated hydrocarbon comprises methane. Optionally, the methane is obtained from natural gas, e.g., wet natural gas. Besides methane, wet natural gas contains a significant amount of a second substantially-saturated hydrocarbon, e.g., $C_2$ to $C_5$ alkane. It is observed that the presence of the second substantially-saturated hydrocarbon in the feed improves methane conversion and yields higher selectivity to liquid products (such as aromatics) at lower reaction temperatures.

Accordingly, one aspect of the present disclosure resides in a process for producing aromatics. The process comprises a first step which includes providing a feed comprising acetylene and at least 9 mole % of a first substantially-saturated hydrocarbon, based on per mole of feed, wherein the molar ratio of substantially-saturated hydrocarbon to acetylene in the feed is in the range of from 0.6:1 to 20:1. The process continues with a second step, which includes contacting the feed with a catalyst comprising at least one molecular sieve component and at least one dehydrogenation component under conditions, including a temperature of at least 300° C., effective to convert at least part of the acetylene and the first substantially-saturated hydrocarbon in the feed to a product comprising at least 5 wt. % of $C_{5+}$ hydrocarbon, such as aromatics, based on the weight of the product. At least a portion of the aromatics can be separated from the product and conducted away from the process, e.g., for storage and/or further processing. Optionally, the first substantially-saturated hydrocarbon comprises ≥90.0 wt. % of methane, based on the weight of the first substantially saturated hydrocarbon. The feed can further comprise at least 9 mole % of a second substantially-saturated hydrocarbon, based on per mole of feed. The second substantially-saturated hydrocarbon can comprise, e.g., ≥90.0 wt. % of alkane, such as one or more $C_2$ to $C_5$ alkane, based on the weight of the second substantially-saturated hydrocarbon. At least part of the methane and $C_2$ to $C_5$ alkane in the feed are optionally derived from natural gas, e.g., from wet natural gas.

In a further aspect, the present disclosure resides in a process for producing aromatics which includes providing a feed comprising acetylene, at least 9 mole % of methane, and at least 9 mole % of one or more $C_2$ to $C_5$ alkane, the mole percents being based on per mole of feed, wherein the molar ratio of methane to acetylene in the feed is in the range of from 0.6:1 to 20:1. The process includes contacting the feed with a catalyst comprising at least one molecular sieve and at least one dehydrogenation component under conditions, including a temperature of at least 300° C., effective to convert at least part of the methane, $C_2$ to $C_5$ alkane, and acetylene in the feed to a product comprising at least 5 wt. % of aromatics, based on the weight of the product. At least part of the aromatics can be separated from the product, e.g., for storage and/or further processing. The molecular sieve can comprise, e.g., one or more aluminosilicate and/or a substituted aluminosilicate having a Constraint Index from 2 to 12, such as ZSM-5 or ZSM-11. The dehydrogenation component can comprise, e.g., at least one metal or compound thereof from Groups 3 to 13 of the Periodic Table, such as a metal or compound thereof selected from Ga, Zn, Cu, Re, Mo, W, La, Fe, Ag, Pt, Pd, and mixtures thereof.

In yet another aspect, the present disclosure resides in a process for producing $C_{5+}$ hydrocarbon. The process includes a first step of contacting a feed comprising methane with an oxygen-containing gas in the presence of a first catalyst under conditions effective to oxidatively couple the methane to produce an effluent containing $C_{2+}$ hydrocarbon and unreacted methane. In a second step, acetylene and at least a portion of the first step's unconverted methane react in the presence of a second catalyst, the second catalyst comprising at least one molecular sieve and at least one dehydrogenation component. The second step's reaction is carried out under conditions effective for converting the acetylene and at least part of the first step's unreacted methane to a product comprising $C_{5+}$ hydrocarbon. Reaction conditions in the second step can include exposing the unreacted methane to a temperature of at least 500° C. Optionally, the entire effluent of the first step is reacted with the acetylene in the second step.

BRIEF DESCRIPTION OF THE DRAWINGS

(FIGS. 1) and 400° C. (FIG. 2), at 1 atmosphere pressure. Aromatics are represented by diamond points. The line through the diamond points represents polynuclear aromatic compounds. The open diamond point represents acetylene. The solid circle point represents graphite. The solid circle with a protruding line (upward protruding line in FIG. 1, downward protruding line in FIG. 2) represents $C_2$ olefin (the circle) and $C_3$ to $C_8$ olefin (the protruding line). Cyclohexane is represented by an "x". $C_{1+}$ normal paraffin is represented by solid rectangles.

DETAILED DESCRIPTION

Definitions

Figure 1:
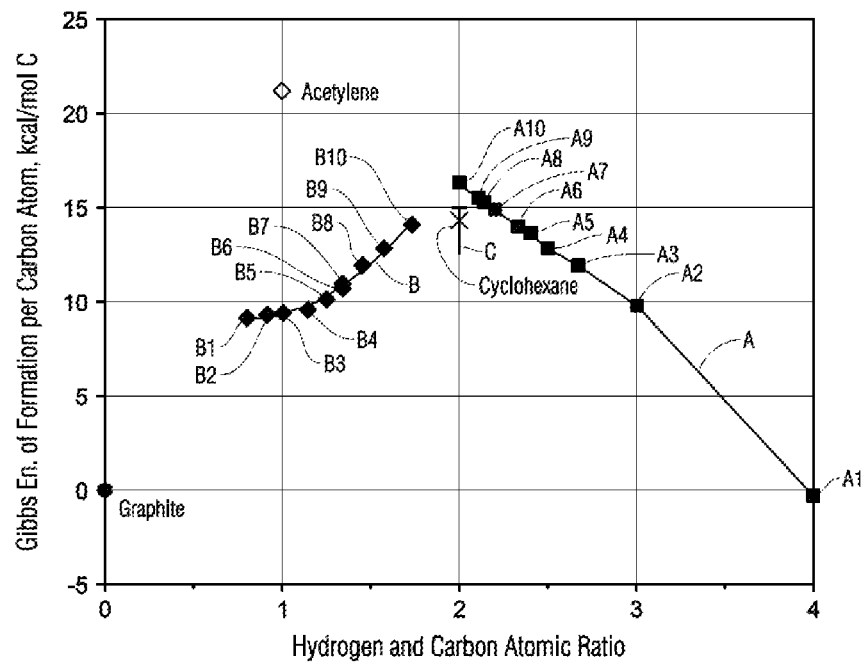
FIGS. 1 and 2 show the Gibbs free energy of formation per carbon atom for exemplary carbon-containing compounds as a function of each compound's hydrogen:carbon H/C atomic ratio at 600° C.

For the purpose of this specification and appended claims, the following terms are defined. The term "Cn" hydrocarbon wherein n is a positive integer, e.g., 1, 2, 3, 4, or 5, means a hydrocarbon having n number of carbon atom(s) per molecule. The term "Cn+" hydrocarbon wherein n is a positive integer, e.g., 1, 2, 3, 4, or 5, means hydrocarbon having at least n number of carbon atom(s) per molecule. The term "Cn−" hydrocarbon wherein n is a positive integer, e.g., 1, 2, 3, 4, or 5, means hydrocarbon having no more than n number of carbon atom(s) per molecule. The term "aromatics" means hydrocarbon molecules containing at least one aromatic core. The term "substantially-saturated hydrocarbon" means hydrocarbon comprising ≤1.0 mole % of molecules which contain at least one double and/or at least one triple bond. The term "hydrocarbon" encompasses mixtures of hydrocarbon, including those having different values of n. As used herein, the numbering scheme for the groups of the Periodic Table of the Elements is as disclosed in Chemical and Engineering News, 63(5), 27 (1985).

The present disclosure relates to producing aromatics by reacting a feed containing acetylene; a first substantially-saturated hydrocarbon, such as methane; and, optionally, a second substantially-saturated hydrocarbon, e.g., $C_2$ to $C_5$ alkane. The feed is reacted in the presence of a catalyst, e.g., a bifunctional catalyst comprising (i) at least one molecular sieve component and (ii) at least one dehydrogenation component. Although the mechanisms of the reactions occurring in the present process are not fully understood, it is believed that substantially-saturated hydrocarbon, such as methane, is activated by the acetylene at the metal and acid sites of the bifunctional catalyst allowing the substantially-saturated hydrocarbon to be aromatized at temperatures ≤700° C., e.g., ≤500° C. In addition, it is found that when (i) the first substantially-saturated hydrocarbon comprises methane and (ii) the feed further comprises a second substantially-saturated hydrocarbon such as $C_2$ to $C_5$ alkane, methane aromatization occurs at even lower temperatures, e.g., ≤475° C.

The advantages achieved by present process are illustrated in Table 1 which lists the Gibbs free energy of formation $\Delta G_{Rxn}$ for the formation of 1 mole of benzene from several different hydrocarbon mixtures. The calculations are carried out using data disclosed in: (i) Stull et al., The Chemical Thermodynamics of Organic Compounds, 1987; (ii) Yaws, C. L., Chemical Properties Handbook, McGraw Hill, 1999.

TABLE 1

| Rxn # | Reaction | Moles of $H_2$ generated per mole of benzene | $\Delta G_{Rxn}$ (kcal/mole benzene) | | | |
|---|---|---|---|---|---|---|
| | | | 300° C. | 500° C. | 650° C. | 800° C. |
| 1 | $6CH_4 \rightarrow C_6H_6 + 9H_2$ | 9 | 75.4 | 49.4 | 28.1 | 5.4 |
| 2 | $4CH_4 + 2/3C_3H_8 \rightarrow C_6H_6 + 23/3H_2$ | 7.7 | 54.2 | 28.2 | 6.9 | −15.8 |
| 3 | $4CH_4 + C_2H_2 \rightarrow C_6H_6 + 6H_2$ | 6 | 18.2 | 6.6 | −3.4 | −14.1 |
| 4 | $CH_4 + C_3H_8 + C_2H_2 \rightarrow C_6H_6 + 4H_2$ | 4 | −13.6 | −25.3 | −35.2 | −45.9 |
| 5 | $4/3C_3H_8 + C_2H_2 \rightarrow C_6H_6 + 10/3H_2$ | 3.3 | −24.1 | −35.9 | −45.8 | −56.5 |
| 6 | $2CH_4 + 2C_2H_2 \rightarrow C_6H_6 + 3H_2$ | 3 | −39.0 | −36.3 | −34.8 | −33.7 |
| 7 | $3C_2H_2 \rightarrow C_6H_6$ | 0 | −96.2 | −79.2 | −66.3 | −53.2 |

Table 1 summarizes the $\Delta G_{Rxn}$ for the formation of 1 mole of benzene, optionally in the presence of one or more of the specified catalyst, from feeds comprising one or more of methane, propane and acetylene. The table shows reaction conditions are more favorable when fewer moles of $H_2$ are generated per mole of benzene, e.g., a specified conversion can be achieved at a lower temperature. In particular, it is observed that acetylene is a more efficient co-reactant than are olefins, and olefins are more efficient co-reactants than are paraffins. For example, the aromatization of pure methane (Rxn No. 1) proceeds at temperatures above 750° C. By contrast, the co-conversion of methane and acetylene to benzene can occur at a much lower temperature, e.g., in the range of from 300° C. to 650° C. (Rxn Nos. 3 and 6). As the relative amount of acetylene in the feed is increased (exemplified by Rxn No. 6), it becomes increasingly desirable to operate the reaction at a relatively low temperature, e.g., in the range of 300° C. to 600° C., such as in the range of 300° C. to 500° C. It is believed that the desirability of low to moderate reaction temperatures at a methane:acetylene molar ratio ≤2.0, e.g., ≤1.0, such as ≤0.5, results from kinetic effects, such as an increase in acetylene-acetylene reactions that are kinetically favored over methane aromatization at temperatures ≥600° C., e.g., ≥650° C., such as ≥700° C., or ≥800° C. The table shows that although the catalytic co-conversion of methane and propane (Rxn No. 2) is more favorable than conversion of methane (Rxn No. 1) and can be carried out above 650° C. ($\Delta G_{Rxn}$, =−0.54 kcal/mole at 700° C.), it is not as thermodynamically favorable as reactions which include acetylene as a co-reactant (see, e.g., Rxn Nos. 3-7). It is observed that other co-reactants, such as one or more paraffins and olefins, react in a way similar to that of Rxn No. 2. Rxn No. 4 and No. 5 show that the favorable thermodynamics arising from the use of an acetylene co-reactant are also attained when a $C_{2+}$ alkane is substituted for at least a portion of the methane as primary reactant. In other words, using acetylene as a co-reactant with methane, methane-paraffin, methane-olefin and methane-paraffin-olefin (e.g. natural gas) mixtures results in more facile reactions, lowering the temperature requirements into the range of from 300° C. to 500° C., e.g., 300° C. to 400° C., such as 300° C. to 350° C., as illustrated by Rxn Nos. 3, 4, 5, and 6.

Figure 2:
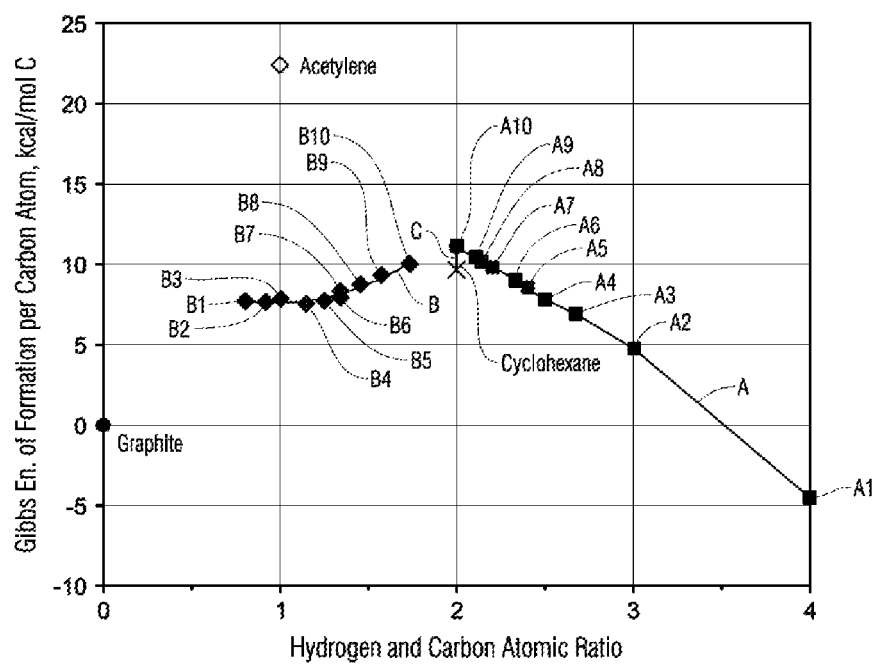

Similarly, FIGS. 1 and 2 qualitatively illustrate the favorable energetics resulting from the use of acetylene as a co-reactant in alkane aromatization. As shown in the figures, blending acetylene with methane (and other light alkane), lessens the average Gibbs free energy of formation. For example, FIG. 1 shows that at 600° C., approximately 10 kcal/mol of carbon is needed for converting methane to benzene. As the figure shows, the favorable energy difference can be provided by an acetylene co-reactant, ≥about 10 kcal/mole of carbon compared to benzene. Energetically, therefore, utilizing acetylene as a co-reactant is far more favorable than using $C_2$ to $C_8$ olefin (a boost of <about 5 kcal/mole carbon) or $C_{23-}$ paraffin (a boost of <about 6 kcal/mole of carbon). FIG. 2 shows that at 400° C., approximately 12 kcal/mole of carbon is needed for converting methane to benzene. As the figure shows, the favorable energy difference can be provided by acetylene co-reactant, ≥15 kcal/mole of carbon compared to benzene. Energetically, therefore, utilizing acetylene as a co-reactant is far more favorable than using $C_2$ to $C_8$ olefin (a boost of <4 kcal/mole carbon) or $C_{23-}$ paraffin (a boost of <3 kcal/mole of carbon). In other words, the figures show that the presence of the acetylene co-reactant more than compensates for the energy change that would otherwise be needed when aromatizing methane. Certain feeds useful in aspects of the invention will now be described in more detail. The invention is not limited to these feeds, and this description is not meant to foreclose the use of other feeds within the broader scope of the invention.

In certain aspects, the feed is primarily in the vapor phase during aromatization, e.g., ≥90.0 wt. % of the feed is in the vapor phase, based on the weight of the feed, such as ≥99.0 wt. %. The feed can comprise acetylene and at least 9 vol. % of a first substantially-saturated hydrocarbon, based on the volume of feed. The first substantially-saturated hydrocarbon can comprise e.g., ≥50.0 wt. % of methane, based on the weight of the first substantially-saturated hydrocarbon, such as ≥75.0 wt. %, or ≥70.0 wt. %, or ≥99.0 wt. %. The molar ratio of first substantially-saturated hydrocarbon to acetylene in the feed can generally be in the range of from 0.6:1 to 20:1, such as from 5:1 to 15:1, for example from 7:1 to 10:1. For example, the molar ratio of methane to acetylene in the feed can be in the range of from 0.6:1 to 20:1, such as from 5:1 to 15:1, for example from 7:1 to 10:1.

Optionally, the feed comprises ≥9 mole % of methane and further comprises ≥0.1 mole %, e.g., ≥9 mole %, of a second substantially-saturated hydrocarbon, the mole percents being based on per mole of feed, wherein the molar ratio of methane to acetylene in the feed being in the range of from 0.6:1 to 20:1. The second substantially-saturated hydrocarbon can comprise, e.g., ≥50.0 wt. % of one or more $C_2$ to $C_5$ alkane, based on the weight of the second substantially-saturated hydrocarbon, such as ≥75.0 wt. %, or ≥90.0 wt. %, or ≥99.0 wt. %. Optionally, the feed further comprises ≥0.1 mole % diluent, based on per mole of feed. Diluent generally comprises species which do not react in significant amounts with substantially-saturated hydrocarbon to produce aromatics under the specified operating conditions. Suitable diluent includes one or more of molecular hydrogen; carbon oxides, such as carbon monoxide, carbon dioxide, and including carbon oxides of non-integral stoichiometry, hydrogen sulfide, and molecular nitrogen. In certain aspects, the feed comprises diluent in an amount in the range of from 0.1 mole % to 50 mole %, based on per mole of feed. Where present, some or all of the diluent can be present as by-products of the process used to produce the feed's acetylene and/or substantially-saturated hydrocarbon.

In certain aspects, the first substantially-saturated hydrocarbon comprises ≥99.0 wt. % of methane, based on the weight of the first substantially-saturated hydrocarbon, and the sole co-reactant in the feed is acetylene. For example, besides acetylene, methane, and diluent, the feed can comprise ≤1.0 mole % of other constituents, based on per mole of feed, e.g., ≤0.1 mole %, such as ≤0.1 mole %. In these aspects, for example, the molar ratio of methane to acetylene in the feed can range from 0.6:1 to 20:1, such as from 5:1 to 15:1, for example from 7:1 to 10:1. Examples of suitable feeds comprise from 80 mole % to 99 mole % of methane and from 1 mole % to 20 mole % acetylene, based on per mole of feed, such as from 85 mole % to 99 vol. % of methane and from 1 mole % to 15 mole % acetylene. The remainder of the feed, if any, can comprise diluent, for example.

In certain aspects, first substantially-saturated hydrocarbon comprises ≥99.0 wt. % of methane, based on the weight of the first substantially-saturated hydrocarbon, and the feed further comprises ≥0.1 mole % of a second substantially-saturated hydrocarbon, based on per mole of feed, e.g., ≥1.0 mole. %, such as ≥10.0 mole %. When, for example, the second substantially-saturated hydrocarbon comprises ≥50.0 wt. % of $C_2$ to Cs alkane, based on the weight of the second substantially-saturated hydrocarbon, e.g., ≥90.0 wt. %, such as ≥99.0 wt. %, then (i) the molar ratio of methane to acetylene in the feed can be in the range of from 0.6:1 to 20:1, such as from 4:1 to 10:1, for example from 5:1 to 10:1; and (ii) the molar ratio of C2 to C5 alkane to acetylene in the feed can be in the range of from 0.1:1 to 20:1 such as from 2:1 to 10:1, for example from 3:1 to 10:1. Examples of suitable feeds comprise from 40 mole % to 80 mole % of methane, from 1 mole % to 15 mole % acetylene and from 1 mole % to 40 mole % $C_2$ to $C_5$ alkane, based on per mole of feed. The remainder of the feed, if any, can comprise diluent, for example.

The source of substantially-saturated hydrocarbon (e.g., the first and/or second substantially-saturated hydrocarbon) is not critical. A preferred source is natural gas, particularly wet natural gas, that is natural gas containing some or all of the higher hydrocarbons, particularly $C_2$ to $C_5$ hydrocarbon, co-produced with methane. A particularly preferred source of natural gas is shale gas. Using the present process, the complex and costly process of separating methane from the higher hydrocarbons present in natural gas can be obviated and the natural gas can be converted to easily transportable liquid hydrocarbons by reaction with acetylene. This facility offers significant advantages in remote or under-developed locations, where the lack of a pipeline or NGL production infrastructure, may result in significant quantities of light hydrocarbon ($C_1$ to $C_4$) resources being burned as fuel rather than being recovered. Small scale plants using the present process would allow effective recovery of these light hydrocarbon resources as liquid hydrocarbons.

Any suitable source of acetylene can be used in the present process. For example, it is known that acetylene is produced as a by-product in the steam cracking of hydrocarbons to produce ethylene and from coal by the calcium carbide process. However, a more preferred source of acetylene is the partial combustion of methane, for example using the process disclosed in U.S. Pat. No. 6,365,792, the entire contents of which are incorporated herein by reference. Another preferred source of acetylene is from the pyrolysis of methane, for example using a reverse flow regenerative reactor system such as is disclosed in U.S. Pat. No. 8,119,076, the entire contents of which are incorporated herein by reference.

A preferred source of both the acetylene and methane is an acetylene generation process that feeds methane or wet natural gas where only a portion of the methane is converted. An even more preferred process is one in which both the acetylene and methane are effluents from an acetylene generation process that feeds methane or wet natural gas where only a portion of the methane is converted and the reactor effluent is close coupled to a second conversion reactor containing a molecular sieve and a dehydrogenation component.

The present process comprises contacting the above-described feed with a catalyst comprising at least one molecular sieve and at least one dehydrogenation component under conditions effective to convert at least part of methane and the acetylene and, where present, the $C_2$ to $C_5$ alkane to aromatics. Such conditions include exposing the feed in the presence of the catalyst to a temperature ≥300° C., e.g., in the range of 300° C. to 700° C., such as in the range of from 350° C. to 650° C., or 400° C. to 500° C. Suitable conditions can further include a pressure in the range of from 110 kPa to 450 kPa (absolute). Feed gas hourly space velocity can be, e.g., ≥200 cm³/h/g of catalyst, such as in the range of 200 cm³/h/g of catalyst to 20,000 cm³/h/g of catalyst. Certain catalysts useful in the invention will now be described in more detail. The invention is not limited to these catalysts, and this description is not meant to foreclose other catalysts within the broader scope of the invention.

In certain aspects, the catalyst comprises at least one medium pore size molecular sieve having a Constraint Index of 2-12 (as defined in U.S. Pat. No. 4,016,218). Examples of such medium pore molecular sieves include ZSM-5, ZSM-11, ZSM-12, ZSM-22, ZSM-23, ZSM-35, ZSM-48 and mixtures and intermediates thereof. ZSM-5 is described in detail in U.S. Pat. No. 3,702,886 and Re. 29,948. ZSM-11 is described in detail in U.S. Pat. No. 3,709,979. A ZSM-5/ZSM-11 intermediate structure is described in U.S. Pat. No. 4,229,424. ZSM-12 is described in U.S. Pat. No. 3,832,449. ZSM-22 is described in U.S. Pat. No. 4,556,477. ZSM-23 is described in U.S. Pat. No. 4,076,842. ZSM-35 is described in U.S. Pat. No. 4,016,245. ZSM-48 is more particularly described in U.S. Pat. No. 4,234,231.

In other aspects, the catalyst employed in the present process comprises at least one molecular sieve of the MCM-22 family As used herein, the term "molecular sieve of the MCM-22 family" (or "material of the MCM-22 family" or "MCM-22 family material" or "MCM-22 family zeolite") includes one or more of:

(i) molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

(ii) molecular sieves made from a common second degree building block, being a 2-dimensional tiling of such MWW framework topology unit cells, forming a monolayer of one unit cell thickness, preferably one c-unit cell thickness;

(iii) molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and (iv) molecular sieves made by any regular or random 2-dimensional or 3-dimensional combination of unit cells having the MWW framework topology.

Molecular sieves of the MCM-22 family include those molecular sieves having an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as incident radiation and a diffractometer equipped with a scintillation counter and associated computer as the collection system.

Materials of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), and mixtures thereof. Related zeolite UZM-8 is also suitable for use as a molecular sieve component of the present catalyst.

In certain aspects, the molecular sieve employed in the present process may be an aluminosilicate or a substituted aluminosilicate in which part of all of the aluminum is replaced by a different trivalent metal, such as gallium or indium.

The invention can be practiced using catalysts that have been subjected to one or more catalyst treatments, e.g., selectivation. For example, the catalyst can comprises at least one molecular sieve which has been selectivated, either before introduction of the catalyst into the reactor or in-situ in the reactor, by contacting the catalyst with a selectivating agent, such as at least one organosilicon in a liquid carrier and subsequently calcining the catalyst at a temperature of 350 to 550° C. This selectivation procedure can be repeated two or more times and alters the diffusion characteristics of the catalyst such that the formation of para-xylene over other xylene isomers is favored. Such a selectivation process is described in detail in U.S. Pat. Nos. 5,633,417 and 5,675,047, the entire contents of which are incorporated herein by reference.

In addition to the molecular sieve component, the catalyst generally comprises at least one dehydrogenation component, e.g., at least one dehydrogenation metal. The dehydrogenation component is typically present in an amount of at least 0.1 wt. %, such as from 0.1 to 5 wt. %, of the overall catalyst. The dehydrogenation component can comprise one or more neutral metals selected from Groups 3 to 13 of the Periodic Table of the Elements, such as Ga, In, Zn, Cu, Re, Mo, W, La, Fe, Ag, Pt, Pd, and/or one or more oxides, sulfides and/or carbides of these metals. The dehydrogenation component can be provided on the catalyst in any manner, for example by conventional methods such as impregnation or ion exchange of the molecular sieve with a solution of a compound of the relevant metal, followed by conversion of the metal compound to the desired form, namely neutral metal, oxide, sulfide and/or carbide. Part or all of the dehydrogenation metal may also be present in the crystalline framework of the molecular sieve.

In one preferred embodiment, the bifunctional catalyst used in the present process is selected from the group consisting of Ga and/or In-modified ZSM-5 type zeolites such as Ga and/or In-impregnated H-ZSM-5, Ga and/or In-exchanged H-ZSM-5, H-gallosilicate of ZSM-5 type structure and H-galloaluminosilicate of ZSM-5 type structure. These zeolites can also be prepared by any suitable method, including conventional methods.

For example, the bifunctional catalyst may contain tetrahedral aluminium and/or gallium, which is present in the zeolite framework or lattice, and octahedral gallium or indium, which is not present in the zeolite framework but present in the zeolite channels in close vicinity to the zeolitic protonic acid sites, and which is attributed to the presence of tetrahedral aluminum and gallium in the catalyst. The tetrahedral or framework Al and/or, Ga is responsible for the acid function of the catalyst and octahedral or non-framework Ga and/or In is responsible for the dehydrogenation function of the catalyst. In one preferred embodiment, the bifunctional catalyst comprises H-galloaluminosilicate of ZSM-5 type structure having framework (tetrahedral) Si/Al and Si/Ga mole ratios of about 10:1 to 100:1 and 15:1 to 150:1, respectively, and non-framework (octahedral) Ga of about 0.5 to 0 wt. %.

In addition to the molecular sieve components and dehydrogenation component, the catalyst may be composited with another material which is resistant to the temperatures and other conditions employed in the conversion reaction. Such materials include active and inactive materials and synthetic or naturally occurring zeolites as well as inorganic materials such as clays and/or oxides such as alumina, silica, silica-alumina, zirconia, titania, magnesia or mixtures of these and other oxides. The latter may be either naturally occurring or in the form of gelatinous precipitates or gels including mixtures of silica and metal oxides. Clays may also be included with the oxide type binders to modify the mechanical properties of the catalyst or to assist in its manufacture. Use of a material in conjunction with the molecular sieve, i.e., combined therewith or present during its synthesis, which itself is catalytically active may change the conversion and/or selectivity of the catalyst. Inactive materials suitably serve as diluents to control the amount of conversion so that products may be obtained economically and orderly without employing other means for controlling the rate of reaction. These materials may be incorporated into naturally occurring clays, e.g., bentonite and kaolin, to improve the crush strength of the catalyst under commercial operating conditions and function as binders or matrices for the catalyst. The relative proportions of molecular sieve and inorganic oxide matrix vary widely, with the sieve content ranging from about 1 to about 90 percent by weight and more usually, when the composite is prepared in the form of beads, in the range of about 2 to about 80 weight percent of the composite.

Conversion of a feed comprising methane and acetylene to aromatics is generally conducted at a temperature of at least 300° C., e.g., a temperature in the range of about 300° C. to 650° C., such as 300° C. to 500° C., or 300° C. to 400° C., or 300° C. to 390° C., or 300° C. to 375° C., or 300° C. to 350° C. In particular aspects the conversion is carried out at a temperature in the range of from 350° C. to 650° C., e.g., from 350° C. to 390° C., or 350° C. to 375° C. The pressure during the conversion is typically in the range of from 110 kPa to 450 kPa (absolute). Where the feed comprises methane, acetylene and also contains $C_2$ to $C_5$ alkane, the aromatics yield is increased even at lower temperatures in this range, particularly in the range of from 300° C. to 500° C., and more particularly in the range of 300° C. to 400° C., and even more particularly in the range of 300° C. to 390° C., or 300° C. to 375° C., or 325° C. to 375° C., or 350° C. to 375° C. The conversion process can be conducted in one or more fixed bed, moving bed or fluidized bed reaction zones. The conversion can be operated, e.g., continuously, semi-continuously, or in batch mode.

The products of the conversion are mainly $C_6$ to $C_{10}$ aromatics and molecular hydrogen, with smaller amounts of ethylene, ethane, propylene, propane, $C_4$ hydrocarbons and traces of $C_{5+}$ aliphatic hydrocarbons (e.g., oligomers). The aromatic product slate tends to be rich in toluene and xylenes, whereas aromatization of acetylene alone favors the production of benzene. The $C_6$ to $C_{10}$ aromatics generally comprise at least 5 wt. % of the product, based on the weight of the product, e.g. ≥10 wt. %, such as ≥15 wt. %. Aromatics can readily be removed from the other conversion products and any residual methane and co-reactants by any convenient method, e.g., well known fractionation and extraction techniques.

Where it is desired to maximize the production of xylenes, it may be advantageous to include an oxygenate, such as syngas and/or alcohol, typically methanol, in the methane containing feed so that most of the benzene and toluene is produced as an intermediate and is then further alkylated via the oxygenate to xylenes. By employing a selectivated catalyst as described above, the relative yield of para-xylene can be increased.

In certain aspects, an Oxidative Coupling of Methane (OCM) is utilized in conjunction with the specified aromatization process. OCM is a process in which methane is reacted with an oxygen-containing gas in the presence of a catalyst, such as an alkaline earth/rare earth metal oxide catalyst, such as Sr-promoted $La_2O_3$, at a temperature of 600 to 800° C. and a pressure is 1 to 10 bar. The reaction is described in, for example, U.S. Pat. No 5,336,825, the entire contents of which are incorporated herein by reference. The process couples the methane into to higher hydrocarbons, such as ethylene, by reactions such as:

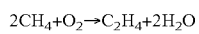

$2CH_4+O_2 \rightarrow C_2H_4+2H_2O$ with a typical $C_2$ yield of 26 to 29% and with about ⅔ of the $C_2$ hydrocarbons being ethylene. The overall product composition from the OCM reaction is 70 mole % to 95 mole % unconverted methane, 5 mole % to 30 mole % olefin, 1 mole % to 5 mole % CO2, and 1 mole % to 5 mole % $H_2O$, the mole percents being per mole of product. Combining OCM with the specified aromatization process, e.g., by operating OCM upstream of the aromatization process, is believed to be beneficial because the olefins can be utilized as a co-reactant with the acetylene to increase the efficiency of the aromatization process over aromatization efficiency using methane and acetylene only.

In certain aspects, the feed to the specified aromatization comprises acetylene and at least a portion of product obtained from OCM, e.g., by diverting away at least a portion of the OCM product toward the aromatization process. For example, the feed's first substantially-saturated hydrocarbon can comprise ≥99.0 wt. % of unconverted methane obtained from OCM, based on the weight of the first substantially-saturated hydrocarbon. Optionally, the feed to the aromatization process comprises acetylene, ≥70 vol. % unconverted methane obtained from OCM, and ≥5 vol. % of olefin, the volume percents being per volume of feed to the aromatization. The balance of the feed, if any, can be diluent, e.g., diluent obtained from OCM product, such as ≥1 vol. % of $CO_2$ and/or ≥1 volume % of H2O. Generally the molar ratio of unconverted OCM methane to acetylene in the feed is in the range of from 0.6:1 to 20:1, such as from 4:1 to 10:1, for example from 5:1 to 10:1. Generally the molar ratio of olefin to acetylene in the feed is in the range of from 0.1:1 to 20:1 such as from 2:1 to 10:1, for example from 3:1 to 10:1. Examples of suitable feeds comprise from 70 mole % to 95 mole % of unconverted OCM methane and 5 mole % to 30 mole % of olefin, based on per mole of feed. The remainder of the feed, if any, can comprise diluent, for example In certain aspects, the total effluent from the OCM reaction zone can be conducted to the aromatization step, e.g., without any intervening separations and preferably without any need for heat exchange (the OCM reaction is exothermic). The second conversion step (the aromatization) can be operated under substantially the same conditions and can utilize substantially the same catalyst, as specified for aromatizing acetylene and the first substantially-saturated hydrocarbon (optionally in combination with the second substantially-saturated hydrocarbon and/or diluent).

In certain aspects, the second step includes oligomerization (instead of or in addition to aromatization), wherein the effluent, from the oligomerization reaction comprises ≥5 wt. % of $C_{5+}$ hydrocarbons, based on the weight of the effluent, such as $C_{5+}$ oligomers of order ≥2. In these aspects, the oligomerization reaction can be exothermic, and methane can be incorporated into the oligomerization reaction. In other aspects, the two steps may be combined into one, with catalytic functionalities for OCM and aromatization or OCM and oligomerization being combined into one catalyst bed and the process being carried out in a single reaction zone.

All patents, test procedures, and other documents cited herein, including priority documents, are fully incorporated by reference to the extent such disclosure is not inconsistent and for all jurisdictions in which such incorporation is permitted.

While the illustrative forms disclosed herein have been described with particularity, it will be understood that various other modifications will be apparent to and can be readily made by those skilled in the art without departing from the spirit and scope of the disclosure. Accordingly, it is not intended that the scope of the claims appended hereto be limited to the examples and descriptions set forth herein but rather that the claims be construed as encompassing all the features of patentable novelty which reside herein, including all features which would be treated as equivalents thereof by those skilled in the art to which this disclosure pertains.

When numerical lower limits and numerical upper limits are listed herein, ranges from any lower limit to any upper limit are contemplated, and are expressly within the scope of the invention. The term "comprising" is synonymous with the term "including". Likewise whenever a composition, an element or a group of components is preceded with the transitional phrase "comprising", it is understood that we also contemplate the same composition or group of components with transitional phrases "consisting essentially of," "consisting of", "selected from the group consisting of," or "is" preceding the recitation of the composition, component, or components, and vice versa.

The invention claimed is:

1. A process for producing $C_{5+}$ hydrocarbon, the process comprising:
   (a) contacting a feed comprising methane with an oxygen-containing gas in the presence of a first catalyst under conditions effective to oxidatively couple the methane to produce an effluent containing $C_{2+}$ hydrocarbons and unconverted methane;
   (b) combining acetylene and at least a portion of the effluent from (a) to produce a second feed, wherein (i) the second feed contains the unconverted methane in an amount of at least 9 mole % based on per mole of the feed, (ii) the second feed contains at least a portion of the $C_{2+}$ hydrocarbon in the effluent, and (iii) the second feed has a molar ratio of the unconverted methane to the acetylene in the range of from 0.6:1 to 20:1;
   (c) contacting the second feed with a second catalyst comprising at least one molecular sieve and at least one dehydrogenation component comprising Ga and/or In under conditions, including a temperature in the range of from 300° C. to 390° C. effective to convert at least a portion of the unconverted methane in the second feed, at least a portion of the acetylene in the second feed, and at least a portion of the $C_{2+}$ hydrocarbon in the second feed to a product comprising at least 5 wt. % of aromatics, based the weight of the product; and
   (d) separating at least part of the aromatics from the product.

2. The process of claim 1, wherein the feed further comprises one or more $C_2$ to $C_5$ alkane.

3. The process of claim 2, wherein at least part of the methane and $C_2$ to $C_5$ alkane in the feed is derived from natural gas.

4. The process of claim 1, wherein the first and second catalysts are contained in the same reaction zone.

* * * * *